(12) United States Patent
Harada et al.

(10) Patent No.: US 6,689,895 B2
(45) Date of Patent: Feb. 10, 2004

(54) 4,8-DODECADIENEDINITRILE AND PROCESS FOR ITS PRODUCTION

(75) Inventors: Katsumasa Harada, Ube (JP); Yasuhisa Fukuda, Ube (JP); Yoshinori Yamanaka, Ube (JP); Tadashi Murakami, Ube (JP); Kenji Hirotsu, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 10/363,415

(22) PCT Filed: Sep. 10, 2001

(86) PCT No.: PCT/JP01/07813

§ 371 (c)(1), (2), (4) Date: Mar. 3, 2003

(87) PCT Pub. No.: WO02/22560

PCT Pub. Date: Mar. 21, 2002

(65) Prior Publication Data

US 2003/0181751 A1 Sep. 25, 2003

(30) Foreign Application Priority Data

Sep. 11, 2000 (JP) .......................... 2000-274724
Sep. 11, 2000 (JP) .......................... 2000-274725

(51) Int. Cl.$^7$ .......................................... C07C 255/09
(52) U.S. Cl. ....................................................... 558/457
(58) Field of Search ........................................ 558/457

(56) References Cited

U.S. PATENT DOCUMENTS 3,637,800 A * 1/1972 Burton et al. ............ 260/465.7

FOREIGN PATENT DOCUMENTS

EP 0 795 542 A 9/1997

OTHER PUBLICATIONS

Bosma et al, "Metathesis of Unsaturated Nitriles", *J. Organomet. Chem.*, vol. 280, No. 1, pp. 115–112 (1985).

* cited by examiner

Primary Examiner—Alan L. Rotman
Assistant Examiner—Ebenezer Sackey
(74) Attorney, Agent, or Firm—Frishauf, Holtz, Goodman & Chick, P.C.

(57) ABSTRACT

The present invention relates to a novel compound 4,8-dodecadienedinitrile represented by the following formula (1):

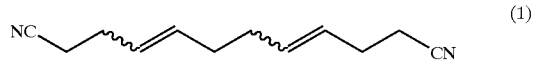

wherein

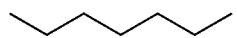

means a cis or trans bond, and a process for preparing 4,8-dodecadienedinitrile which comprises reacting a 2-alkoxy-5,9-cyclododecadienone oxime or a 2-halogeno-5,9-cyclododecadienone oxime with formic acid and hydroxylamine.

5 Claims, 4 Drawing Sheets

4,8-DODECADIENEDINITRILE AND PROCESS FOR ITS PRODUCTION

This application is a U.S. National Phase Application under 35 U.S.C. 371 of International Application No. PCT/JP01/07813 (not published in English) filed Sep. 19, 2001.

TECHNICAL FIELD

The present invention relates to a novel compound, 4,8-dodecadienedinitrile and a process for preparing the same, more specifically it is to provide a novel compound, 4,8-dodecadienedinitrile which is an intermediate for the preparation of 1,12-dodecanedicarboxylic acid or 1,12-dodecanediamine, etc. useful as a starting material for nylon 12 and a process for preparing the same.

BACKGROUND ART

The novel compound of the present invention can be used as an intermediate for the preparation of 1,12-dodecanedicarboxylic acid or 1,12-dodecanediamine, etc. useful as a starting material for nylon 12.

The compound of the present invention has never been known and is a novel compound.

An object of the present invention is to provide a novel compound, 4,8-dodecadienedinitrile.

SUMMARY OF THE INVENTION

The present invention relates to a novel compound, 4,8-dodecadienedinitrile represented by the following formula (1):

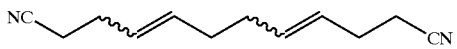

wherein

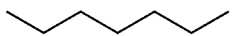

each means a cis or trans bond.

Also, the process for preparing the above-mentioned compound of the present invention comprises reacting a 2-alkoxy-5,9-cyclododecadienone oxime or a 2-halogeno-5,9-cyclododecadienone oxime with formic acid and hydroxylamine.

BRIEF DESCRIPTION OF THE DRAWINGS

FIG. 1 shows the mass spectrum of 4,8-dodecadienedinitrile,

BEST MODE FOR CARRYING OUT THE INVENTION

Figure 1A:
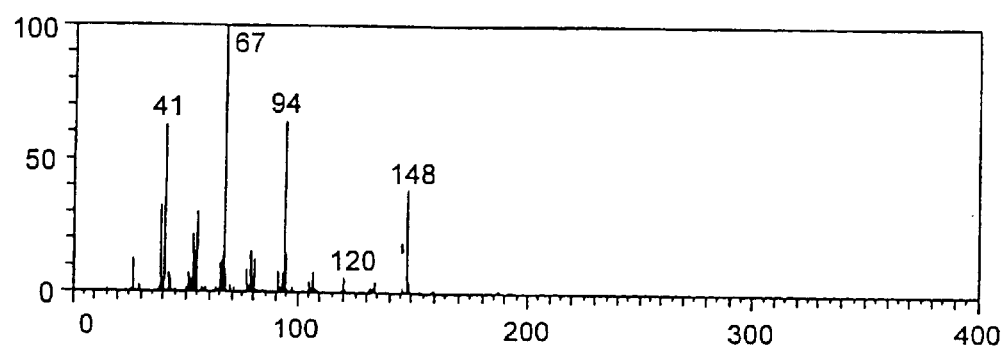
FIG. 1(a) is the EI-MS spectrum of 4,8-dodecadienedinitrile.

In the following, the present invention is explained in more detail.

A novel compound, 4,8-dodecadienedinitrile of the present invention has two double bonds, so that some isomers are present, and any of the compounds having a structure of a cis, trans isomer, a trans, trans isomer, and a cis, cis isomer, etc., are included in the present invention.

The novel compound, 4,8-dodecadienedinitrile of the present invention can be prepared, for example, from a 2-alkoxy-5,9-cyclododecadienone oxime or a 2-halogeno-5,9-cyclododecadienone oxime with formic acid and hydroxylamine.

The novel compound, 4,8-dodecadienedinitrile was separated and purified, and then, its chemical structure was determined by various kinds of instrumental analyses.

More specifically, it was determined by (1) mass spectrometric analysis (MS)
(2) proton nuclear magnetic resonance analysis ($^1$H-NMR)
(3) infrared spectroscopic analysis (IR) and
(4) carbon nuclear magnetic resonance analysis ($^{13}$C-NMR).

As one example of specific examples of a process for preparing 4,8-dodecadienedinitrile, it can be obtained by using a 2-alkoxy-5,9-cyclododecadienone oxime or a 2-halogeno-5,9-cyclododecadienone oxime as a starting material and reacting it with formic acid and hydroxylamine.

The 2-alkoxy-5,9-cyclododecadienone oxime shown as an example can be obtained by the reaction of a 2-halogeno-5,9-cyclododecadienone oxime and an alcohol, and in Japanese Patent Publication No. 45-19902 (19902/1970), a process for preparing a 2-alkoxycyclododecadienone oxime has been disclosed. In said publication, there is disclosed that α-chloro oxime is treated in an alcohol, particularly in a primary alcohol with ammonia at 0 to 100° C., preferably at 10 to 50° C. whereby an alicyclic α-alkoxy oxime can be obtained.

Incidentally, in the 2-alkoxy-5,9-cyclododecadienone oxime or the 2-halogeno-5,9-cyclododecadienone oxime, there exist two double bonds, so that some isomers are present. It may be any structure such as a cis isomer and a trans isomer. These isomers may be used as a mixture without causing any problem.

Also, the 2-alkoxy-5,9-cyclododecadienone oxime or the 2-halogeno-5,9-cyclododecadienone oxime may be used as a commercially available product or a synthesized product as such, or may be used as a purified product by crystallization, etc. without causing any problem.

As an alkoxy group of the 2-alkoxy-5,9-cyclododecadienone oxime, it is not specifically limited and preferably an alkoxy group having 1 to 4 carbon atoms, particularly preferably a methoxy group. Also, as a halogeno group of the 2-halogeno-5,9-cyclododecadienone oxime, there may be mentioned a fluorine atom, a chlorine atom, a bromine atom and an iodine atom, particularly preferably a chlorine atom.

Formic acid to be used in the present invention is not specifically limited and a usual commercially available product can be used, and anhydrous formic acid or hydrated formic acid may be used. Preferably formic acid of 50% by weight or more can be used, more preferably that of 70% by weight or more may be used.

An amount of the formic acid to be used is preferably 0.2 to 100 parts by weight, more preferably 2.5 to 40 parts by weight based on the amount of the 2-alkoxy-5,9-cyclododecadienone oxime or the 2-halogeno-5,9-cyclododecadienone oxime used as a starting material.

The hydroxylamine to be used in the present invention may be used a material itself or a salt thereof. As the salt thereof, it is not specifically limited, and a salt such as hydrochloride, sulfate, phosphate, nitrate, oxalate, etc., is commercially available and they can be used as such.

An amount thereof is usually 0.1 to 10-fold moles, preferably 0.8 to 2-fold moles based on the amount of the 2-alkoxy-5,9-cyclododecadienone oxime or the 2-halogeno-5,9-cyclododecadienone oxime.

In the present invention, when the 2-halogeno-5,9-cyclododecadienone oxime is used as a starting material, it is preferred to use ammonia and/or an amine compound as a dehalogenating agent.

A method of adding ammonia is not specifically limited, and an aqueous ammonia solution may be used. With regard to a concentration of the aqueous ammonia solution, it is not specifically limited, and a usual commercially available product may be used. Or else, an ammonia gas may be directly introduced into the reaction system. Moreover, an ammonium salt may be added to the reaction system.

Specific examples of the ammonium salt may include ammonium carbonate, ammonium formate, an ammonium salt of an organic carboxylic acid and the like.

The amine compound is a compound in which at least one of hydrogen atoms of the ammonia is replaced by a hydrocarbon residue, and preferably there may be mentioned an aliphatic amine compound having 1 to 4 carbon atoms. Specific examples of such an amine compound may include methylamine, dimethylamine, trimethylamine, ethylamine, diethylamine, triethylamine and the like.

An amount of the ammonia and/or the amine compound to be used is preferably 0.8-fold mole or more, more preferably 1 to 10-fold moles, particularly preferably 1 to 5-fold moles based on an amount of the 2-halogeno-5,9-cyclododecadienone oxime.

As a reaction solvent of the present invention, a formic acid solution is usually used as such, and an organic solvent may be also used. As the organic solvent, it is not specifically limited so long as it is a solvent inactive to the present reaction, and there may be mentioned an aliphatic alcohol such as methanol, ethanol, and the like, a nitrile such as acetonitrile, propionitrile, and the like, an aliphatic halogenated hydrocarbon such as methylene chloride, carbon tetrachloride, and the like, an ether such as diethyl ether, dioxane, and the like, an aliphatic hydrocarbon such as hexane, heptane, and the like, an aromatic hydrocarbon such as benzene, toluene, chlorobenzene, and the like, an aliphatic carboxylic acid such as acetic acid, propionic acid, and the like. An amount of these solvent to be used is usually 0 to 100-fold weight, preferably 0 to 50-fold weight based on an amount of the 2-alkoxycycloalkanone oxime.

The reaction temperature is not specifically limited so long as the reaction is carried out at a boiling point or less of the reaction solvent to be used, and the reaction may be generally carried out at 20 to 200° C., preferably at 40 to 110° C.

Also, the reaction is usually carried out under a normal pressure, and may be practiced under a slight pressurization.

The reaction apparatus is also not specifically limited, and it may be carried out by a reactor equipped with a usual stirring device.

The reaction time may vary depending on the reaction conditions such as the above-mentioned concentration, temperature, and the like, and generally 0.05 to 24 hours.

The novel compound, 4,8-dodecadienedinitrile obtained in the present invention can be separated and purified by distillation, crystallization and the like.

The novel compound, 4,8-dodecadienedinitrile obtained in the present invention can be converted into 1,12-dodecanedicarboxylic acid by hydrogenation of the double bond according to the conventionally known technique and then subjecting to hydrolysis, or may be converted into 1,12-dodecanediamine by hydrogenation of the double bond and two cyano groups.

Not only these dicarboxylic acids and diamines are used as a starting material for nylon 12 but also the dicarboxylic acids are used as a starting material for a polyester.

EXAMPLES

Next, the present invention will be explained by referring to Examples but the present invention is not limited by these.

Example 1

In 50 ml of 99% by weight formic acid were dissolved 0.6 g (2.7 mmol) of 2-methoxy-5,9-cyclododecadienone oxime and 0.59 g (8.5 mmol) of hydroxylamine hydrochloride and the mixture was refluxed for 30 minutes.

After completion of the reaction, formic acid was removed under reduced pressure, and water was added to the obtained residue and the mixture was extracted with toluene twice. The organic layer was washed with 2N sodium hydroxide twice and brine, and then, dried over anhydrous sodium sulfate. After filtration, the solvent was removed under reduced pressure and the residue was purified by column chromatography (Wakogel C-200, toluene: ethyl acetate=20:1) to obtain 0.41 g (2.2 mmol) of 4,8-dodecadienedinitrile which is a colorless oily product. The yield was 81%.

Figure 1B:
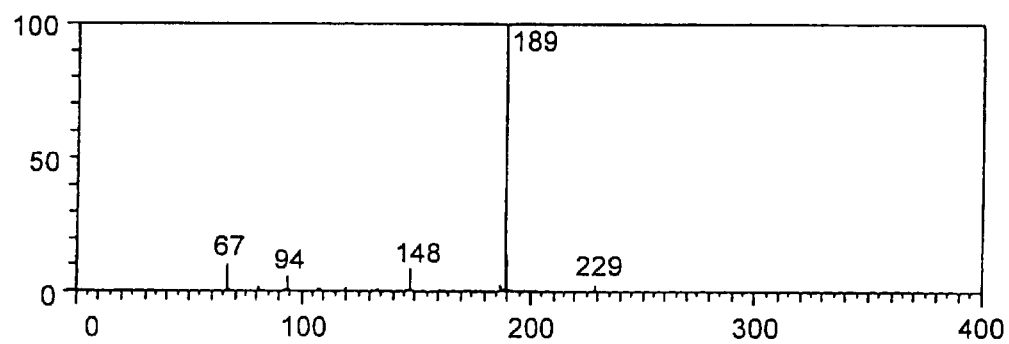
FIG. 1(b) is the CI-MS spectrum of 4,8-dodecadienedinitrile.
Figure 2:
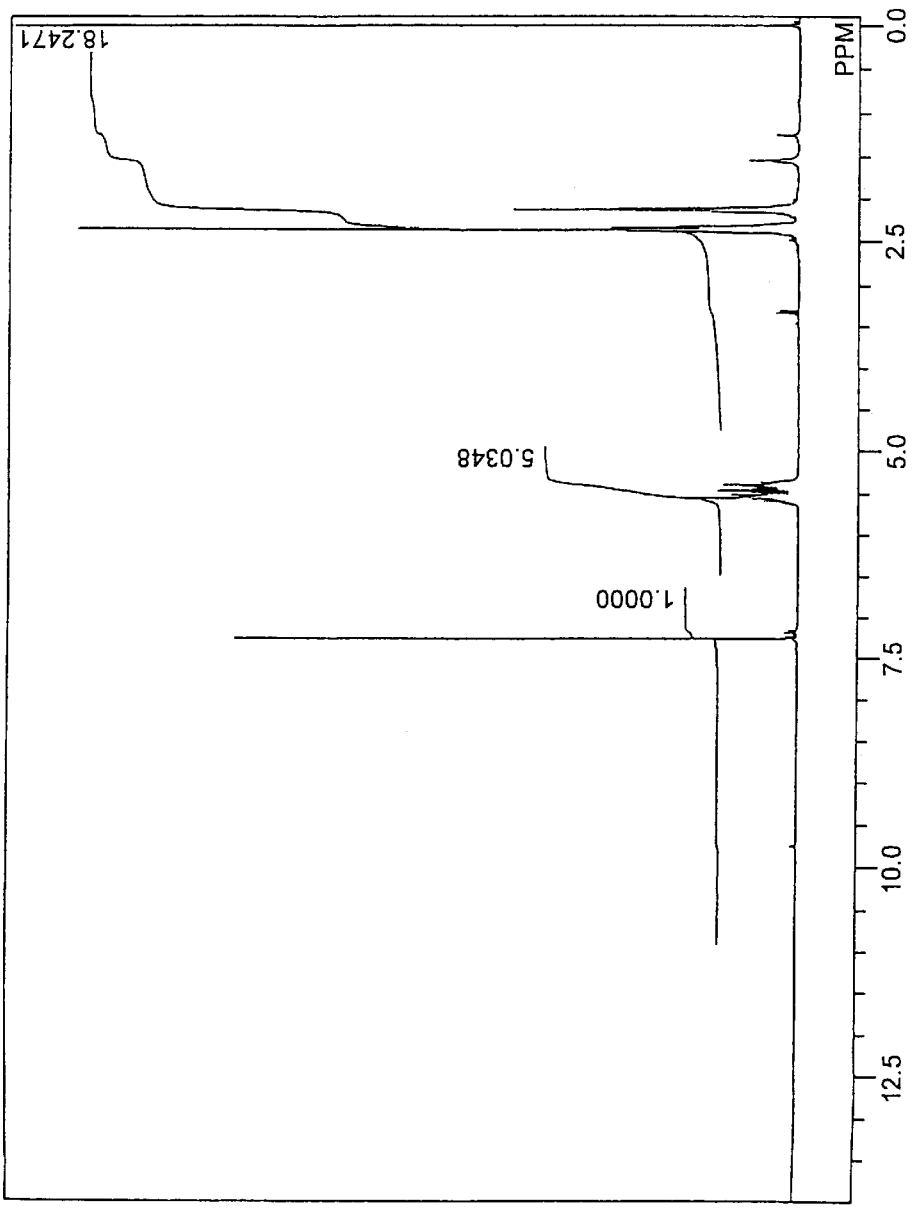
FIG. 2 shows the proton nuclear magnetic resonance spectrum of 4,8-dodecadienedinitrile.
Figure 3:
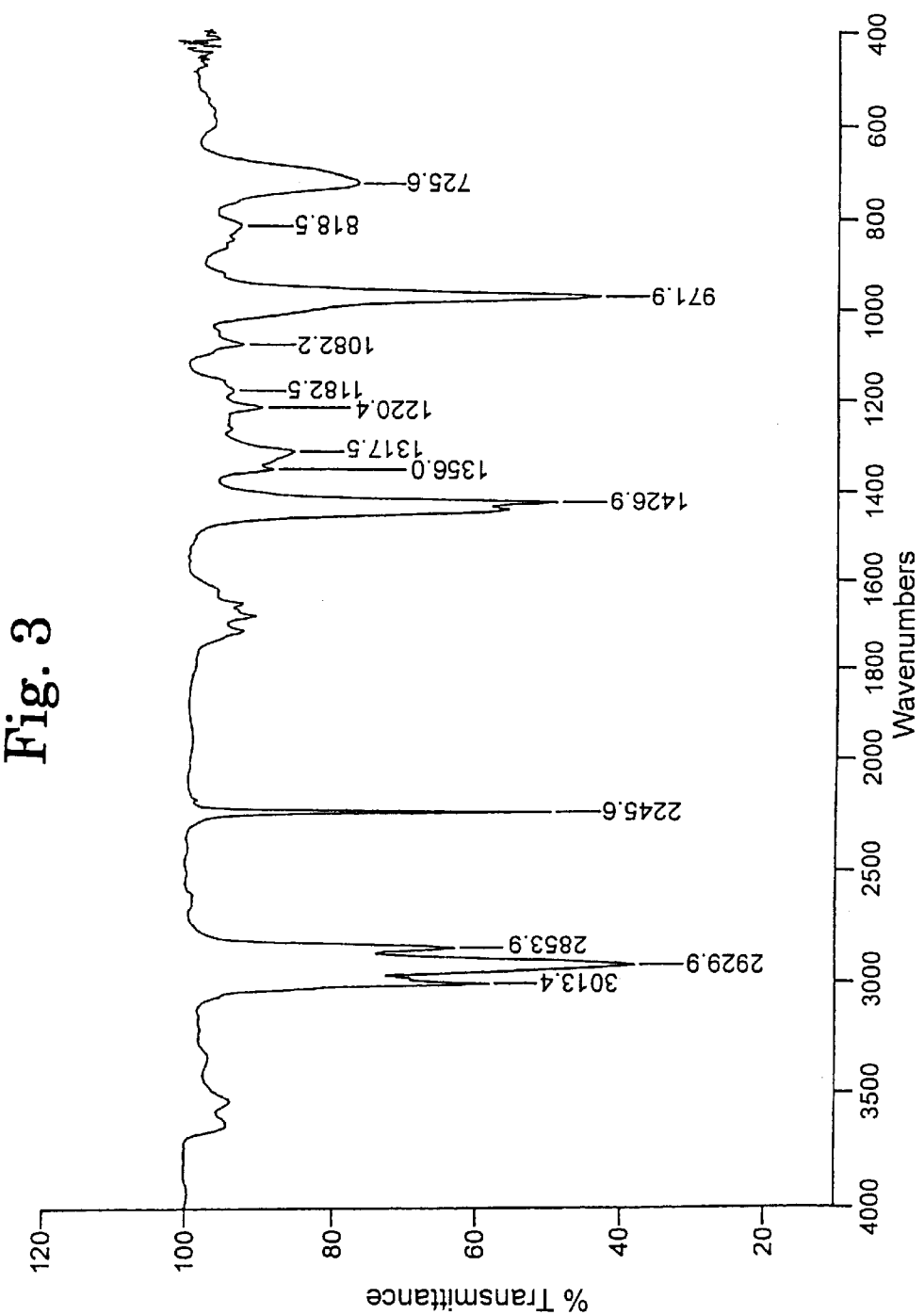
FIG. 3 shows the infrared spectrum of 4,8-dodecadienedinitrile.
Figure 4:
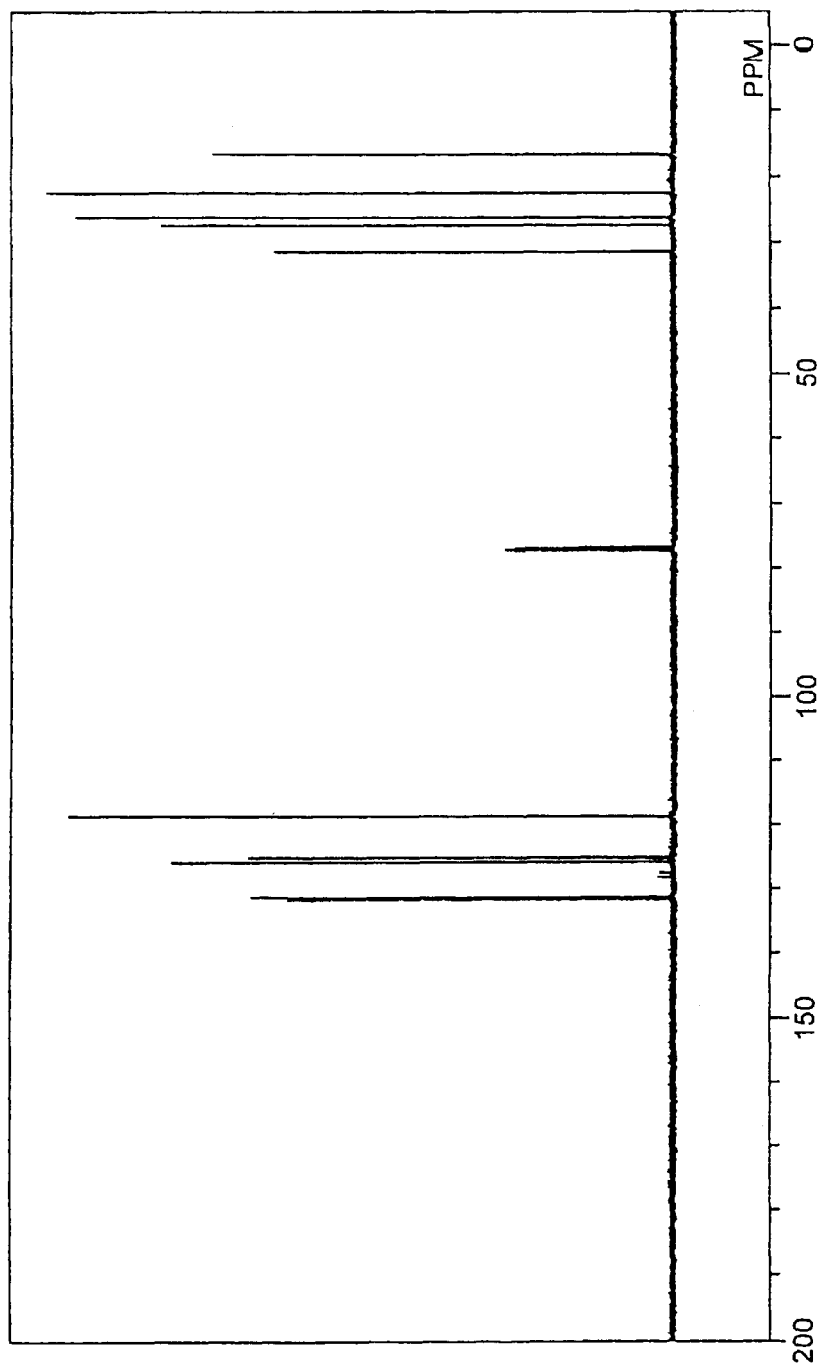
FIG. 4 shows the carbon nuclear magnetic resonance spectrum of 4,8-dodecadienedinitrile.

Results of various kinds of instrumental analyses of the 4,8-dodecadienedinitrile which is a colorless oily product are as follows.
(1) Mass Spectrometric Analysis (MS) (FIG. 1)
m/z (EI) 148, 94, 67
m/z (CI) 189 (MH$^+$)
(2) Proton Nuclear Magnetic Resonance Analysis ($^1$H-NMR) (FIG. 2)
$^1$H-NMR (300 MHz, CDCl$_3$) δ: 2.10 to 2.22 (4H, m), 2.32 to 2.50 (8H, m), 5.35 to 5.64 (4H, m)
(3) Infrared Spectroscopic Analysis (IR) (FIG. 3).
IR (cm$^{-1}$): 2245 (—CN), 1449, 1427, 972, 726
(4) Carbon Nuclear Magnetic Resonance Analysis ($^{13}$C-NMR) (FIG. 4)
$^{13}$C-NMR (200 MHz, CDCl$_3$) δ: 16.5, 16.6, 22.4, 26.1, 27.4, 31.3, 118.7, 118.8, 125.1, 125.9, 131.3, 131.7

Example 2

In 25 ml of 99% by weight formic acid were dissolved 0.3 g (1.4 mmol) of 2-methoxy-5,9-cyclododecadienone oxime and 0.2 g (2.9 mmol) of hydroxylamine hydrochloride, and the mixture was refluxed for 30 minutes.

After completion of the reaction, formic acid was removed under reduced pressure, water was added to the obtained residue and the mixture was extracted with toluene twice. The organic layer was washed with a saturated aqueous sodium bicarbonate solution twice and brine, and then, dried over anhydrous sodium sulfate. After filtration, the solvent was removed under reduced pressure to obtain a yellowish oily product. The obtained oily product was dissolved in acetonitrile, and then, quantitatively analyzed by high performance liquid chromatography (HPLC). As a result, it was found that 0.24 g (1.3 mmol, yield: 93%) of 4,8-dodecadienedinitrile had been contained.

Example 3

In 10 ml of 90% by weight formic acid were dissolved 0.5 g (2.2 mmol) of 2-methoxy-5,9-cyclododecadienone oxime and 0.2 g (1.2 mmol) of hydroxylamine sulfate, and the mixture was refluxed for 30 minutes.

After completion of the reaction, formic acid was removed under reduced pressure, water was added to the obtained residue and the mixture was extracted with diethyl ether twice. The organic layer was washed with a saturated aqueous sodium bicarbonate solution twice and brine, and then, dried over anhydrous sodium sulfate. After filtration, the solvent was removed under reduced pressure to obtain a yellowish oily product. The obtained oily product was dissolved in acetonitrile and quantitatively analyzed by HPLC. As a result, it was found that 0.36 g (1.9 mmol, yield: 86%) of 4,8-dodecadienedinitrile had been formed.

Example 4

In 5.0 g of 75% by weight formic acid were dissolved 0.5 g (2.2 mmol) of 2-chloro-5,9-cyclododecadienone oxime, 0.2 g (1.2 mmol) of hydroxylamine sulfate and 0.31 g (4.6 mmol) of 25% aqueous ammonia, and the mixture was refluxed for 30 minutes.

After completion of the reaction, formic acid was removed under reduced pressure, water was added to the obtained residue and the mixture was extracted with toluene twice. The organic layer was washed with water once and brine, and then, dried over anhydrous sodium sulfate. After filtration, the solvent was removed under reduced pressure to obtain a yellowish oily product. The obtained oily product was dissolved in acetonitrile and quantitatively analyzed by HPLC. As a result, it was found that 0.35 g (1.86 mmol, yield: 85%) of 4,8-dodecadienedinitrile had been formed.

Example 5

In 2.5 g of 75% by weight formic acid were dissolved 0.5 g (2.2 mmol) of 2-chloro-5,9-cyclododecadienone oxime, 0.2 g (1.2 mmol) of hydroxylamine sulfate and 0.17 g (2.5 mmol) of 25% aqueous ammonia, and the mixture was refluxed for 30 minutes.

After completion of the reaction, the post-treatment was carried out in the same manner as in Example 4. As a result of quantitative analysis by HPLC, it was found that 0.34 g (1.8 mmol, yield: 82%) of 4,8-dodecadienedinitrile had been formed.

Example 6

In 2.5 g of 75% by weight formic acid were dissolved 0.5 g (2.2 mmol) of 2-chloro-5,9-cyclododecadienone oxime, 0.2 g (1.2 mmol) of hydroxylamine sulfate and 0.31 g (4.6 mmol) of 25% aqueous ammonia, and the mixture was refluxed for 30 minutes.

After completion of the reaction, the post-treatment was carried out in the same manner as in Example 4. As a result of quantitative analysis by HPLC, it was found that 0.30 g (1.6 mmol, yield: 73%) of 4,8-dodecadienedinitrile had been formed.

Example 7

In 2.5 g of 75% by weight formic acid were dissolved 0.5 g (2.2 mmol) of 2-chloro-5,9-cyclododecadienone oxime, 0.2 g (1.2 mmol) of hydroxylamine sulfate and 0.29 g (4.6 mmol) of ammonium formate, and the mixture was refluxed for 30 minutes.

After completion of the reaction, the post-treatment was carried out in the same manner as in Example 4. As a result of quantitative analysis by HPLC, it was found that 0.33 g (1.8 mmol, yield: 80%) of 4,8-dodecadienedinitrile had been formed.

Example 8

In 2.5 g of 75% by weight formic acid were dissolved 0.5 g (2.2 mmol) of 2-chloro-5,9-cyclododecadienone oxime, 0.2 g (1.2 mmol) of hydroxylamine sulfate and 0.46 g (4.6 mmol) of triethylamine, and the mixture was refluxed for 30 minutes.

After completion of the reaction, the post-treatment was carried out in the same manner as in Example 4. As a result of quantitative analysis by HPLC, it was found that 0.31 g (1.6 mmol, yield: 73%) of 4,8-dodecadienedinitrile had been formed.

Example 9

In 2.5 g of 99% by weight formic acid were dissolved 0.5 g (2.2 mmol) of 2-chloro-5,9-cyclododecadienone oxime, 0.2 g (1.2 mmol) of hydroxylamine sulfate and 0.31 g (4.6 mmol) of 25% aqueous ammonia, and the mixture was refluxed for 30 minutes.

After completion of the reaction, the post-treatment was carried out in the same manner as in Example 4. As a result of quantitative analysis by HPLC, it was found that 0.29 g (1.56 mmol, yield: 71%) of 4,8-dodecadienedinitrile had been formed.

Utilizability in Industry

According to the present invention, a novel compound, 4,8-dodecadienedinitrile can be provided. This novel compound can be used as an intermediate for the preparation of 1,12-dodecanedicarboxylic acid or 1,12-dodecanediamine and the like which are available as a starting material for nylon 12.

What is claimed is:

1. 4,8-Dodecadienedinitrile represented by the following formula (1):

wherein

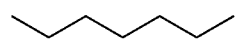

means a cis or trans bond.

2. 4,8-Dodecadienedinitrile according to claim 1, wherein it is a cis, trans isomer.

3. 4,8-Dodecadienedinitrile according to claim 1, wherein it is a trans, trans isomer.

4. 4,8-Dodecadienedinitrile according to claim 1, wherein it is a cis, cis isomer.

5. A process for preparing 4,8-dodecadienedinitrile which comprises reacting a 2-alkoxy-5,9-cyclododecadienone oxime or a 2-halogeno-5,9-cyclododecadienone oxime with formic acid and hydroxylamine.

* * * * *